United States Patent
Cage et al.

(10) Patent No.: US 9,364,589 B2
(45) Date of Patent: Jun. 14, 2016

(54) METHOD OF MAKING A COATED WIRE GUIDE

(71) Applicants: Logan Michael Cage, Bloomington, IN (US); James Cameron Elsesser, Bloomington, IN (US)

(72) Inventors: Logan Michael Cage, Bloomington, IN (US); James Cameron Elsesser, Bloomington, IN (US)

(73) Assignee: COOK MEDICAL TECHNOLOGIES LLC, Bloomington, IN (US)

(*) Notice: Subject to any disclaimer, the term of this patent is extended or adjusted under 35 U.S.C. 154(b) by 0 days.

(21) Appl. No.: 14/593,647

(22) Filed: Jan. 9, 2015

(65) Prior Publication Data

US 2015/0132468 A1    May 14, 2015

Related U.S. Application Data

(62) Division of application No. 12/723,770, filed on Mar. 15, 2010, now abandoned.

(60) Provisional application No. 61/159,916, filed on Mar. 13, 2009.

(51) Int. Cl.
| | |
|---|---|
| *A61L 31/00* | (2006.01) |
| *B05D 1/26* | (2006.01) |
| *B05D 3/00* | (2006.01) |
| *A61L 31/10* | (2006.01) |
| *A61M 25/09* | (2006.01) |
| *B05D 5/00* | (2006.01) |

(52) U.S. Cl.
CPC .............. *A61L 31/10* (2013.01); *A61M 25/09* (2013.01); *B05D 1/265* (2013.01); *B05D 3/002* (2013.01); *B05D 5/00* (2013.01); *A61L 2420/02* (2013.01); *A61M 2025/09108* (2013.01); *A61M 2025/09133* (2013.01)

(58) Field of Classification Search
CPC ........... A61M 2025/09133; A61M 2025/0915; A61M 25/09
USPC ........... 600/585; 427/2.1, 331, 348, 256, 261, 427/267, 282, 271
See application file for complete search history.

(56) References Cited

U.S. PATENT DOCUMENTS

| | | |
|---|---|---|
| 5,213,111 A | 5/1993 | Cook et al. |
| 5,722,424 A | 3/1998 | Engelson |
| 5,756,144 A | 5/1998 | Wolff et al. |
| 5,772,609 A | 6/1998 | Nguyen et al. |
| 5,836,893 A | 11/1998 | Urick |
| 5,984,878 A | 11/1999 | Engelson |
| 6,461,311 B2 | 10/2002 | DuBois et al. |
| 6,488,637 B1 | 12/2002 | Eder et al. |
| 7,014,616 B2 | 3/2006 | Ferrera |

(Continued)

FOREIGN PATENT DOCUMENTS

JP        01310772 A  * 12/1989

*Primary Examiner* — Cachet Sellman
(74) *Attorney, Agent, or Firm* — Brinks Gilson & Lione

(57) ABSTRACT

In a method for making a wire guide, a fluoropolymer coating is removed from a distal section of an FP coated core wire to expose a metallic portion. A polymer coating is applied to a proximal section of the FP coated core wire such that the polymer coating overlays at least a portion of the FP coating, and to the distal section of the FP coated core wire including the exposed metal portion. The polymer coating is removed from the FP coating to form the wire guide having a proximal portion with the FP coating and a distal portion with the polymer coating. A hydrophilic coating may be applied to the distal portion over the polymer coating.

12 Claims, 6 Drawing Sheets

(56) References Cited

U.S. PATENT DOCUMENTS

| | | |
|---|---|---|
| 7,097,624 B2 | 8/2006 | Campion et al. |
| 7,115,101 B2 | 10/2006 | Cornelius et al. |
| 7,455,646 B2 | 11/2008 | Richardson et al. |
| 2004/0185179 A1* | 9/2004 | Connors, III ......... A61M 25/01 427/402 |
| 2006/0047224 A1* | 3/2006 | Grandfield ............ A61M 25/09 600/585 |
| 2006/0282016 A1 | 12/2006 | Cornelius et al. |
| 2007/0293791 A1 | 12/2007 | Lee et al. |
| 2008/0146967 A1 | 6/2008 | Richardson et al. |
| 2010/0268265 A1 | 10/2010 | Krolik et al. |
| 2011/0160680 A1 | 6/2011 | Cage et al. |

* cited by examiner

_US 9,364,589 B2_

METHOD OF MAKING A COATED WIRE GUIDE

CROSS REFERENCE TO RELATED APPLICATIONS

This application is a Divisional of U.S. application Ser. No. 12/723,770, filed Mar. 15, 2010, and claims priority to and all available benefits of U.S. Provisional Patent Application No. 61/159,916, filed Mar. 13, 2009, and which is hereby incorporated by reference in its entirety.

TECHNICAL FIELD

The present invention relates to a method of making medical devices. More particularly, the invention relates to a method for making a coated wire guide.

BACKGROUND

Often elongated, flexible wire guides are used to gain access to specific inner areas of the body. The wire guide may enter the body through a small opening and travel to parts of the body through body channels. For example, wire guides may be passed through the body via peripheral blood vessels, gastrointestinal tract, or the urinary tract. Wire guides are commercial available and are currently used in cardiology, gastroenterology, urology, and radiology. Once in place at a desired location in the body, wire guides are commonly used as guides for the introduction of additional medical instruments, e.g., catheters.

One design challenge for wire guides is that the wire guide provides minimal force for being advanced through the vasculature of a patient. The wire guide must also provide sufficient tactile feedback in order to allow the interventionalist to feel wire movement. Minimizing the force required for advancing the wire guide through the patient's body while retaining sufficient tactile feedback for feeling wire movement, however, are two properties which for the most part are diametrically opposed to one another. That is, minimizing the force required for advancing the wire guide usually involves a decrease in the tactile feedback from moving the wire guide. Accordingly, further improvements and enhancements for wire guides are desirable.

SUMMARY

In at least one embodiment of the present invention, a method for making a wire guide is provided. The method comprises providing a core wire having a fluoropolymer (FP) coating disposed thereon defining a FP coated core wire. A distal section of the FP coated core wire comprises an exposed metal portion. A polymer coating is applied to a proximal section of the FP coated core wire such that the polymer coating overlays at least a portion of the FP coating and to the distal section of the FP coated core wire such that the polymer coating overlays the exposed metal portion. The polymer coating is removed from the proximal section of the FP coated core wire to form the wire guide having a proximal portion with the FP coating and a distal portion with the polymer coating. A hydrophylic coating may be applied to the polymer coating.

Further objects, features, and advantageous of the present invention will become apparent from consideration of the following description and appended claims when taken in conjunction with the accompanying drawings.

DETAILED DESCRIPTION OF THE DRAWINGS

Detailed embodiments of the present invention are disclosed herein. It is understood, however, that the disclosed embodiments are merely exemplary of the invention and may be embodied in various and alternative forms. The figures are not necessarily to scale; some figures may be configured to show the details of a particular component. Therefore, specific structural and functional details disclosed herein are not to be interpreted as limiting but merely as a representative basis for the claims and teaching one skilled in the art to practice the present invention.

Examples of the present invention seek to overcome some of the concerns associated with providing a wire guide for guiding various medical devices through a body channel or cavity of a patient while reducing force for advancing the wire guide through the channel or cavity with sufficient tactile feedback in order to allow the interventionalist to feel wire movement.

Employing the principles of the present invention is, for example, a wire guide, a method for making the wire guide and a catheter kit. The wire guide comprises a core wire having at least two distinct coatings disposed thereon. By having the two distinct coatings, the properties of the coatings can be respectively selected to provide corresponding sections of the wire guide with different properties. In one example, the wire guide has a proximal section coated with fluoropolymer (FP) coating, such as for example, a polytetrafluoroethylene (PTFE) coating. The lubricity of the FP coating is sufficiently tactile to allow the interventionalist to feel wire movement. In another example, the wire guide has a distal section with a polymer coating covered by a hydrophilic coating. The polymer coating provides adhesion for the hydrophilic coating to the distal section (e.g. polymer coating acts as a primer and/or adhesion promoter) and the hydrophilic coating provides relatively high lubricity to minimize the force necessary for advancing the wire guide through the body channel or cavity.

Figure 1A:
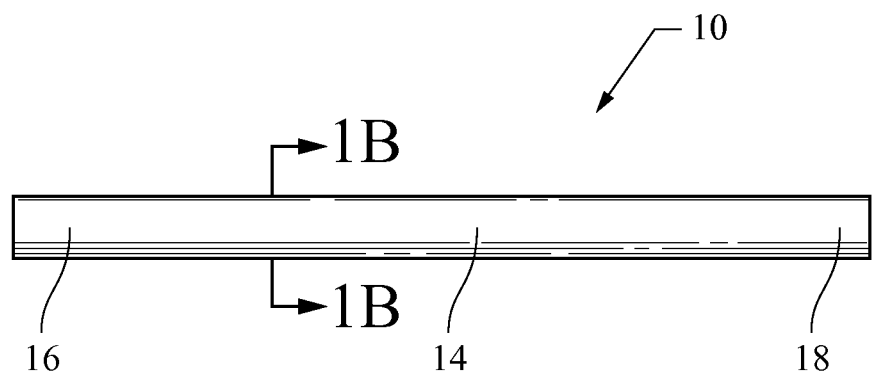
FIG. 1A is a side view of a core wire in accordance with an embodiment of the present invention.
Figure 1B:
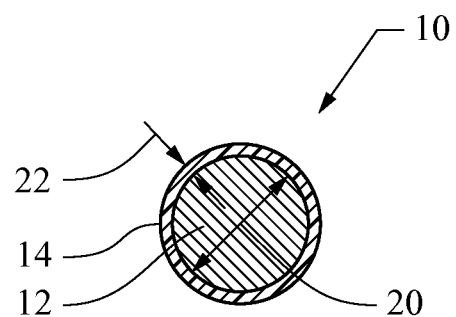
FIG. 1B is a cross-sectional view of the core wire depicted in FIG. 1A.

Referring to FIGS. 1A-1B, a FP coated core wire 10 for use in making a wire guide in accordance with at least one embodiment of the present invention is provided. The fluoropolymer (FP) coated core wire 10 has a proximal section 16 extending to a distal section 18 and is formed from a core wire 12 that is coated with a FP coating 14.

The core wire 12 may be comprised of a material that is relatively stiff and more kink resistant such as stainless steel, or alternatively, a material that is relatively more flexible such as nitinol. Other metallic materials known to those skilled in the art may also be used to make the core wire 12.

The core wire 12 may be made by any suitable wire forming process, such as for example, pultrusion or extrusion of a metal alloy through a mold or die that has a substantially circular opening. The core wire 10 preferably has an elongated cylindrical form with a corresponding diameter 20. Various diameters 20 for the core wire 12 are within the scope and spirit of the present invention with many medical procedures preferably having wire guides with a core wire diameter 20 not exceeding about 0.020 inches (20 mil). The core wire 12 may also have a variable diameter to form a FP coated core wire 10 with a relatively flexible portion and a relatively stiff portion.

The FP coating 14 may be applied to the core wire 12 by any suitable process, such as for example, spray, extrusion, brush or dip coating. A heating process may also be used to facilitate curing and/or cross-linking of the FP coating 14. A coating thickness 22 of the FP 14 is typically on the order of between about 0.2 mil to 1 mil, however, larger or small thicknesses may be used without departing from the scope and spirit of the present invention.

Figure 2:
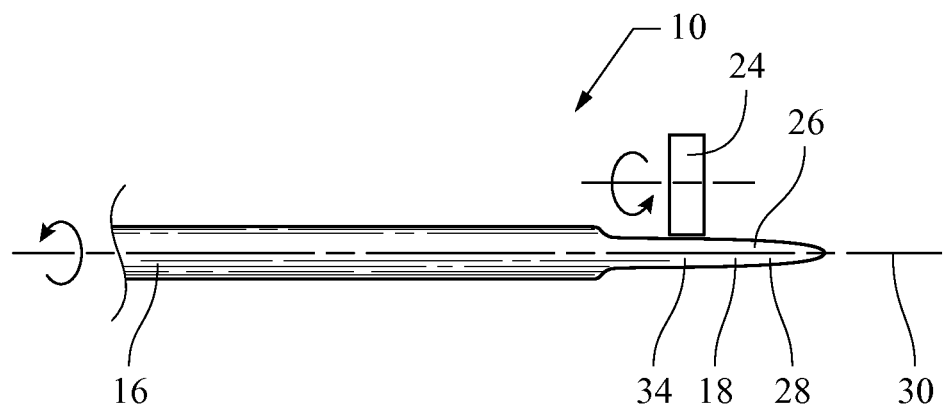
FIG. 2 is a side view of a core wire being machined in accordance with one embodiment of the present invention.
Figure 3:
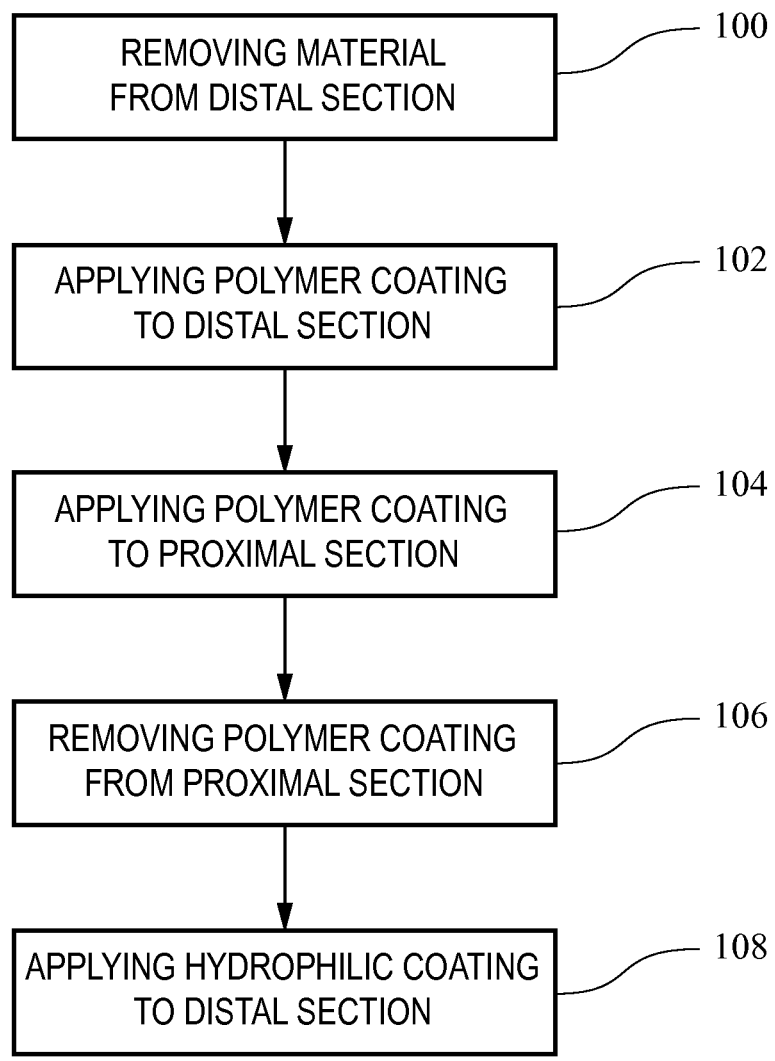
FIG. 3 is a flow chart for a method of making a wire guide in accordance with one example of the present invention.

Referring to FIGS. 2 and 3, an example of a method for making a wire guide is provided. Material is removed at 100 from the distal section 18 of the FP coated core wire 10, for example, by machining or grinding with a grinding wheel 24. In particular, the FP coating 14 is removed from the distal section 18 by the machining process to expose the underlying metal material 26 of the core wire 12. Preferably, a portion of the metal core wire 12 is also removed during the grinding process. Other suitable methods for stripping the FP coating 14 from the distal section 18 to expose a metal portion of the metal core wire 12 may also be used, such as for example, chemical etching or sand blasting. Alternatively, the FP coated core wire 10 may be fabricated such that the FP coating 14 is only applied to the proximal section 16 or along selective areas of the proximal section 16 of the core wire 12, leaving the metal material 26 exposed in the non-FP coated areas.

The machining or grinding process is preferably capable of machining away material from the FP coated core wire 10 to produce intricate shapes with varying diameters and geometries. Accordingly, the grinding wheel 24 may be accurately controlled for movement over numerous axes. In one example, this is accomplished by using an automated computer numerically controlled (CNC) multi-axis grinding machine. Preferably the CNC grinding machine is capable of controlled movement over at least two axes, e.g., the X and Y axis. The grinding machine may also interface directly with a CAD/CAM and include a fully integrated multi-axis servo controller. This arrangement may allow for machining of very intricate shapes which have been designed using a CAD based program. In one example, the grinding machine is capable of machining a shape within the FP coated core wire 10 to within several microns of a targeted dimension.

Figure 4A:
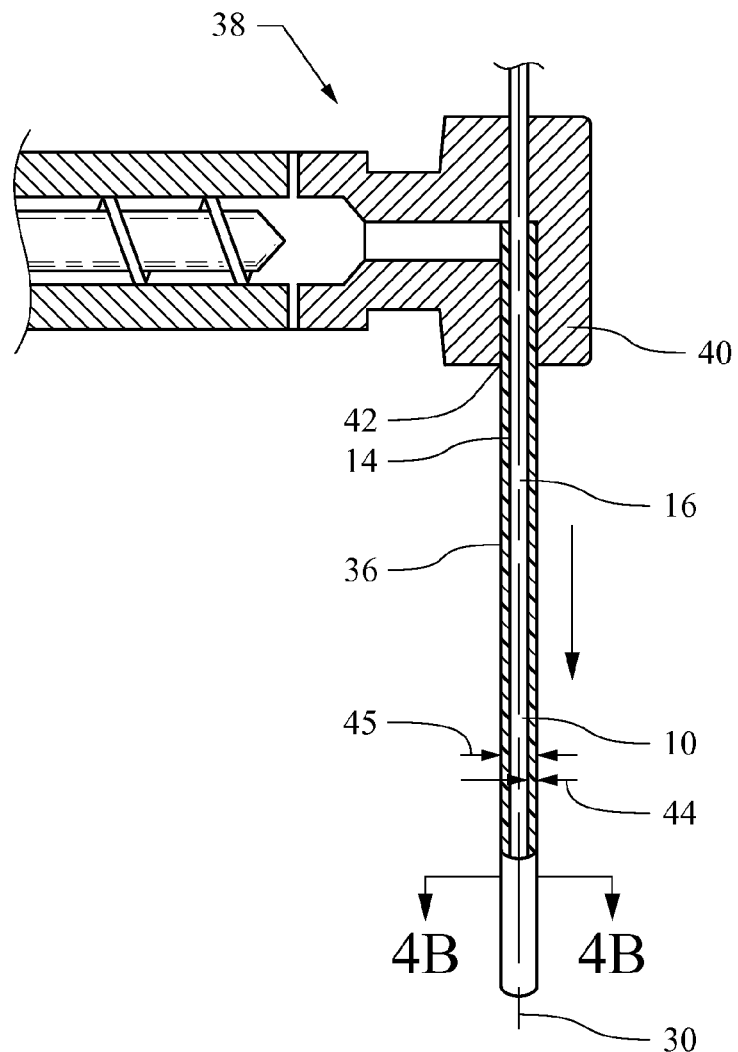
FIG. 4A is a sectional side view of core wire being coated in accordance with one embodiment of the present invention.
Figure 4B:
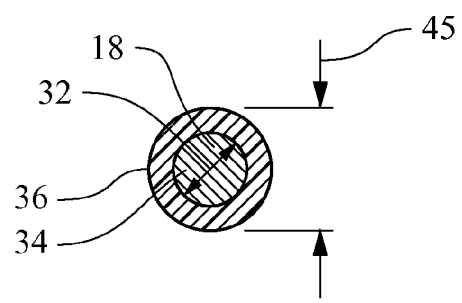
FIG. 4B is a cross-sectional view of the coated core wire depicted in FIG. 4A.
Figure 5A:
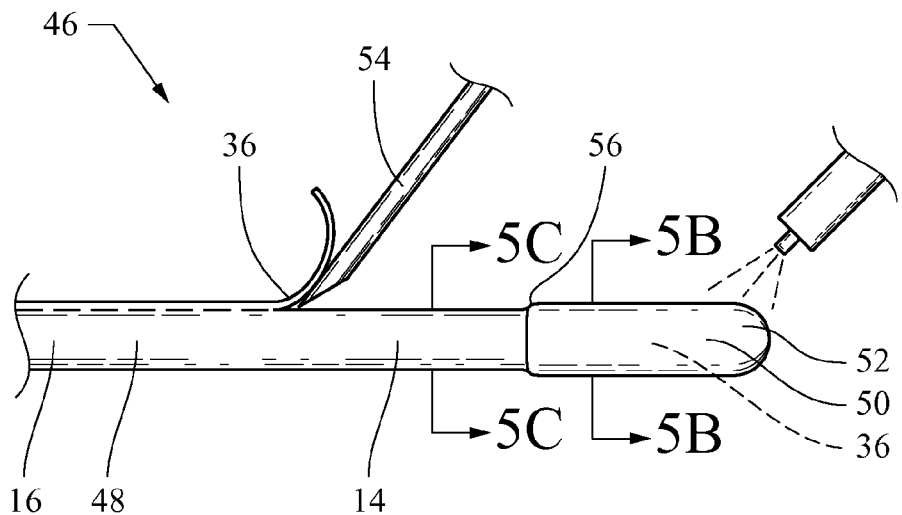
FIG. 5A is a side view of a wire guide in accordance with an embodiment of the present invention.
Figure 5B:
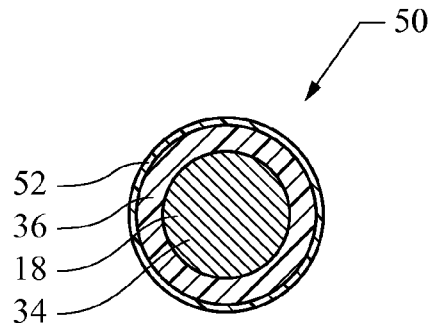
FIG. 5B is a cross-sectional view of the wire guide depicted in FIG. 5A.
Figure 5C:
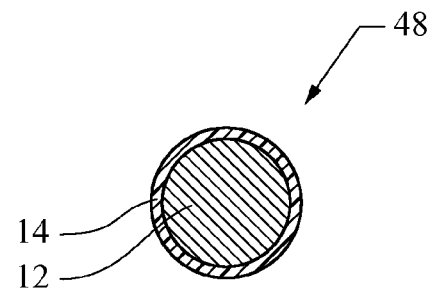
FIG. 5C is a cross-sectional view of the wire guide depicted in FIG. 5A.
Figure 6A:
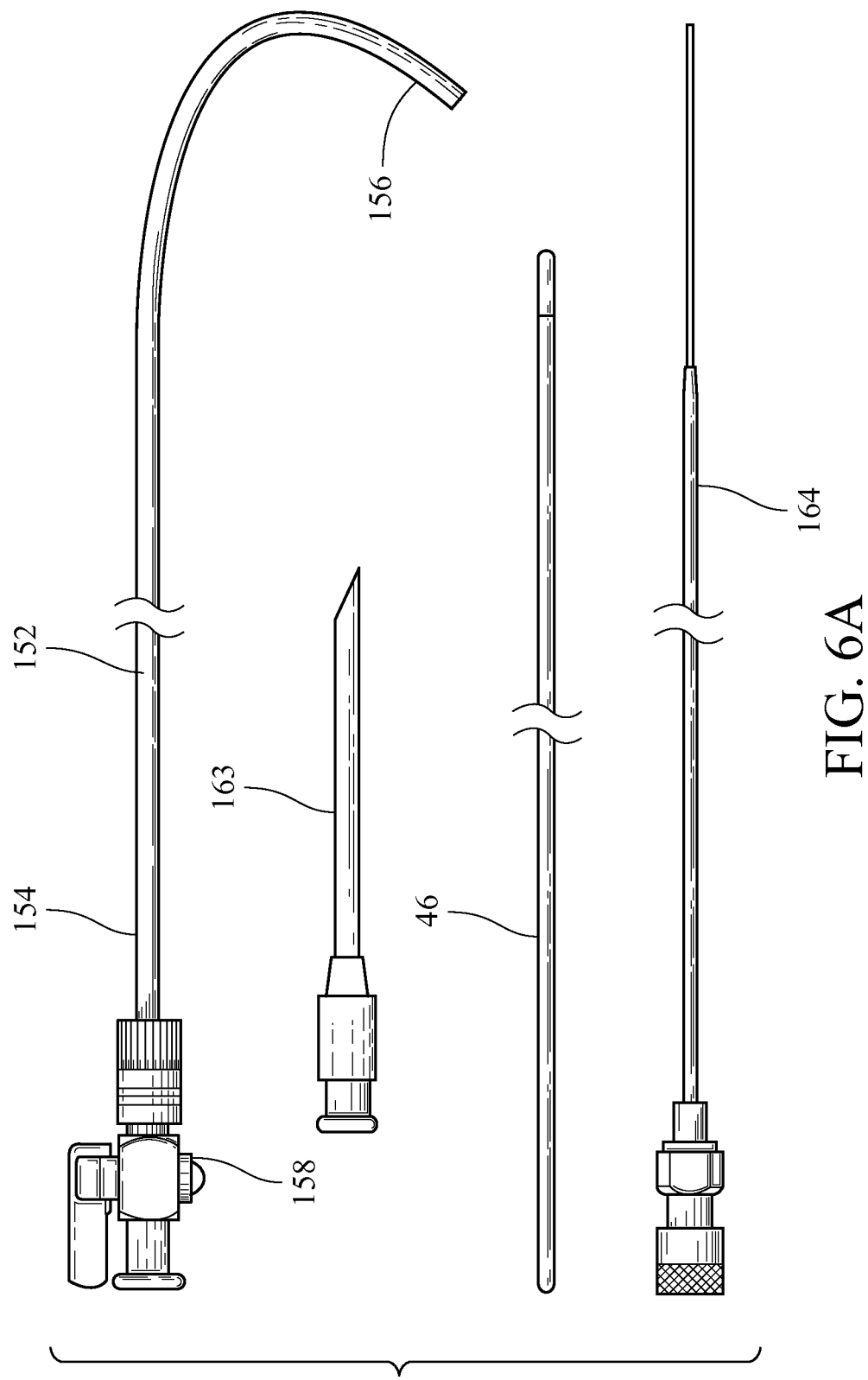
FIG. 6A is an exploded view of a catheter kit in accordance with one embodiment of the present invention.
Figure 6B:
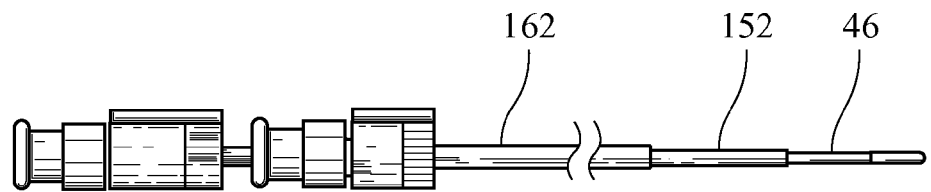
FIG. 6B is a side view of a catheter kit in accordance with an embodiment of the present invention.
Figure 6C:
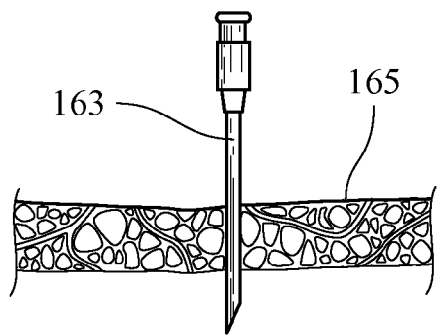
FIG. 6C is a side view of a needle from a catheter kit in accordance with one embodiment of the present invention.
Figure 6D:
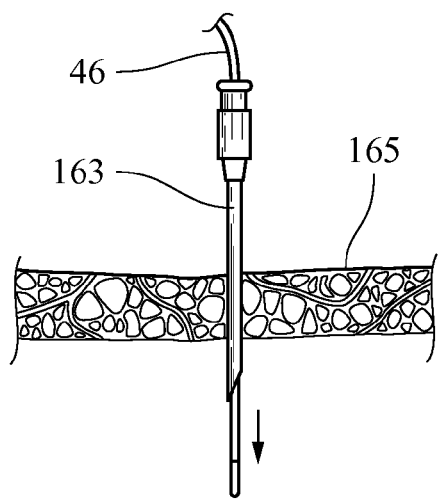
FIG. 6D is a side view of a needle and a wire guide of a catheter kit in accordance with an embodiment of the present invention.

In one embodiment, the distal section 18 of the FP coated core wire 10 is machined while being rotated along its longitudinal axis 30 to form substantially circular cross sections along the distal section 18 with corresponding diameters 32 (Shown in FIG. 4B). The diameters 32 are configured to vary along the distal section 18 to define the shape of the distal section 18. In one embodiment, the variable diameter 32 is configured to taper distally to form a tapered distal tip 34 as shown in FIG. 2. In one example, the variable diameter 32 varies substantially linearly along the distal section 18 to form a partial cone shape or frustoconical section. Alternatively, the variable diameter 32 may vary in a non-linear fashion along the distal section 18.

Referring to FIGS. 3-4B, a polymer coating 36 is applied at 102, 104 over the machined distal section 18 (e.g. tapered tip 34) and the proximal section 16 of the FP coated core wire 10. As illustrated, the polymer coating 36 is applied over the FP coated core wire 10 via an extrusion die arrangement 38 that includes a die 40. The die 40 has an opening 42 that is substantially circular with a larger diameter than the diameter 20 of the FP coated core wire 10. The longitudinal axis 30 of the FP coated core wire 10 is aligned with the opening 42 and the FP coated core wire 10 is advanced through the die 40 and the opening 42 to apply the polymer coating 36 thereon at a predetermined thickness 44 and outer diameter 45 corresponding to the die opening 42. In at least one embodiment, the thickness 44 of the polymer coating 36 is between about 0.5 and 10 mil.

As mentioned in the foregoing paragraphs, the machined distal section 18 includes the exposed metal material 26 or portion of the core wire 12 and accordingly, the polymer coating 36 is applied over at least a portion of the exposed metal material 26. In one embodiment, the polymer coating 36 is in direct contact with the metal material 26 and is made of a material that adhesively bonds or affixes to the metal 26. The polymer coating 36 may be a thermoplastic polymer or alternatively, a thermoset polymer. For example, a thermoplastic polymer coating 36 can be applied to the FP coated core wire 10 at a temperature above its melting point ($T_m$). The thermoplastic is then cooled below its $T_m$ to form a solid polymer layer bonded to the metal material 26 of the distal section 18. In another example, a thermosetting polymer coating 36 (e.g. pre-polymer or thermoset precursor) is applied to the FP coated core wire 10 and is heated to a suitable temperature for curing or cross-linking the polymer coating 36. The cured or cross-linked polymer forms a solid layer bonded to the metal material 26 of the distal section 18. Various polymeric materials may be used to form the polymer coating 36 including polyurethanes, polyesters, polyamides, polyethylene, polystyrene, polyether block amides or a mixture thereof. Moreover, the polymer coating 36 may contain a filler material such as radiopacifier, e.g., tungsten, bismuth and/or barium sulfate. Other suitable material know to those in the art may also be used.

In at least one embodiment, the polymer coating 36 is applied over the proximal section 16 of the FP coated core wire 10 and is in direct contact with the FP coating 14. The polymer coating 36 preferably has little or no adhesion to the FP coating once the polymer coating 26 is cooled and/or cured about the proximal section 16. In one example, minimal adhesion between the FP coating 14 and the polymer coating 36 is achieved by using a polymer coating 36 that has at least about 10 dynes/cm greater surface energy that the FP coating 14. It is believed that the relatively lower surface energy of the FP coating 14 provides sufficiently high surface tension between the FP coating 14 and the polymer coating 36 to reduce adhesion of the polymer coating 36 to the proximal section 16.

Referring to FIGS. 3 and 5A-5C, the polymer coating 36 is removed at 106 from the proximal section 16 of the FP coated core wire 10 to form a wire guide 46. The wire guide 46 has a proximal portion 48 with the FP coating 14 and a distal portion 50 with the polymer coating 36.

As illustrated, a stripping device 54 may be used to remove the polymer coat 36. The stripping device 54 may be any suitable device for applying a shear and/or abrasive force to the polymer coating 36 for its removal. Preferably, the polymer coating 36 is stripped only from the proximal section 16 and remains on the distal section 18, forming an edge 56 that is adjacent to the FP coating 14. The edge 56 may be configured as a slight step (e.g. 0.5 to 5 mil) between the proximal and distal portions 48 and 50, and forms a transition between the two distinct coatings 14 and 36 disposed on the wire guide 46.

Moreover, Applicants have found that by minimizing the adhesion between the FP and polymer coatings 14 and 36, removal of the polymer coating 36 from the proximal section 16 is facilitated. It is believed that minimizing the force for removing the polymer coating 36 reduces the potential for damage to the FP coating, which in one example, forms an exterior surface of the proximal portion 48. In a preferred embodiment, the FP coating 14 comprises polytetrafluoroethylene (PTFE) which has provided excellent results in trials for removing the polymer coating 36 from the FP coating 14. However, other suitable FP coatings 14 may be used, such as for example, fluorinated ethylene-propylene (FEP), polyethylenetetrafluoroethylene (ETFE), perfluoroalkoxy polymer (PFA), polyvinylfluoride (PVF), polyethylenechlorotrifluoroethylene (ECTFE), and/or polyvinylidene fluoride (PVDF).

In one embodiment, a hydrophilic coating 52 is applied at 108 over the polymer coating 36 disposed about the distal section 18. The polymer coating 36 preferably acts as a primer or adhesion promoter between the metal material 26 and the hydrophilic coating 52. In one example, the hydrophilic coating 52 comprises polyvinylpyrrolidones, polyethylene oxides, polyacrylates or a mixture thereof. The hydrophilic coating 52 may be applied to the polymer coating 36 by any suitable process known to those skilled in the art including spray, extrusion, brush or dip coating. In one example, the hydrophilic coating 52 forms an exterior surface of the distal portion 50 of the wire guide 46. Preferably, the hydrophilic coating 52 has a lubricity with a coefficient of friction that is relatively lower than the coefficient of friction of the FP coating 36, thereby providing the wire guide 46 with two distinct exterior coatings 36 and 52 corresponding to the proximal and distal portions 48 and 50.

Referring to FIGS. 6A-6D, a catheter kit 150 for accessing a body channel or cavity is provided. As shown, the kit 150 includes a microcatheter 152 preferably made of a soft, flexible material such as silicone or any other suitable material. Generally, the microcatheter 152 has a proximal end 154, a distal end 156, and a plastic adapter or hub 158 to receive a medical device (not shown), e.g., angioplasty balloon, stent, occluding device, etc., to be advanced therethrough. In this embodiment, the inside diameter of the microcatheter 152 may range between 0.014 and 0.027 inches.

The kit 150 further includes the wire guide 46 as discussed in the foregoing paragraphs. The wire guide 46 provides a guide catheter 162 a path during insertion of the guide catheter 162 within the body channel or cavity. The size of the wire guide 46 is based on the inside diameter of the guide catheter 162. A needle 163 may also be provided for percutaneously introducing the wire guide 46 into a patient 165.

The guide catheter 162 or sheath is typically made of polytetrafluoroethylene (PTFE) and is for percutaneously introducing the microcatheter 152 into the body of the patient 165. Of course, any other suitable material may be used without falling beyond the scope or spirit of the present invention. The guide catheter 162 may have a size of about 4-French to 8-French and allows the microcatheter 152 to be inserted therethrough to a desired location in the body channel or cavity. The guide catheter 162 receives the microcatheter 152 and provides stability of the microcatheter 152 at a desired location within the body. For example, the guide catheter 162 may stay stationary within a common visceral artery, e.g., a common hepatic artery, and adds stability to the microcatheter 152 as the microcatheter 152 is advanced through the guide catheter 162 to a desired point in a connecting artery, e.g., the left or right hepatic artery.

When the distal end 156 of the microcatheter 152 is at the desired point in the body, the medical device may be loaded at the proximal end 154 of the microcatheter 152 and is advanced through the microcatheter 152 for deployment through the distal end 156. In one embodiment, a push wire 164 is used to mechanically advance or push the medical device through the microcatheter 152.

It is to be understood that the catheter kit 150 described above is merely one example of a kit that may be used with the wire guide 46. Of course, other kits, assemblies, and systems may be used with the wire guide 46 without falling beyond the scope or spirit of the present invention.

As a person skilled in the art will readily appreciate, the above description is meant as an illustration of the implementation of the principles of this invention. This description is not intended to limit the scope of application of this invention in that the invention is susceptible to modification, variation, and change, without departing from the spirit of this invention, as defined in the following claims.

What we claim is:

1. A method for making a wire guide comprising:
   providing a metal core wire having a fluoropolymer (FP) coating disposed thereon defining a FP coated core wire having a proximal section adjoining a distal section,
   removing the FP coating from the distal section of the core wire to form an exposed metal portion;
   applying a polymer coating to the distal section including the exposed metal portion and to the proximal section such that the polymer coating overlays the exposed metal portion and at least a portion of the FP coating; and
   removing the polymer coating from the FP coating to form the wire guide having a proximal portion with the FP coating remaining on the core wire and a distal portion with the polymer coating.

2. The method according to claim 1 wherein the step of applying the polymer coating to the proximal section includes extruding the polymer coating over the FP coating, and the step of applying the polymer coating to the distal section includes extruding the polymer coating over the exposed metal portion.

3. The method according to claim 1 wherein the polymer coating comprises polyurethanes, polyesters, polyamides, polyethylene, polystyrene, polyether block amides or a mixture thereof, and the FP coating comprises polytetrafluoroethylene (PTFE), fluorinated ethylene-propylene (FEP), polyethylenetetrafluoroethylene (ETFE), perfluoroalkoxy polymer (PFA), polyvinylfluoride (PVF), polyethylenechlorotrifluoro-ethylene (ECTFE), polyvinylidene fluoride (PVDF) or a mixture thereof.

4. The method according to claim 1 wherein the step of removing the polymer coating includes stripping the polymer coating from the FP coating such that the polymer coating remains on the exposed metal portion and forms an edge bordering the FP coating.

5. The method according to claim 1 wherein the step of removing the FP coating includes machining the distal section of the FP coated core wire to form a distally tapered metallic end portion.

6. The method according to claim 5 wherein the step of machining the distal section of the FP coated core wire includes machining the metallic core to form the distally tapered metallic end portion.

7. The method according to claim 1 further comprising applying hydrophilic coating to the distal section over the polymer coating.

8. The method according to claim 7 wherein the FP coating and the hydrophilic coating form respectively a proximal exterior surface and a distal exterior surface of the wire guide, and wherein a coefficient of friction of the distal exterior surface is relatively lower than a coefficient of friction of the proximal exterior surface.

9. The method according to claim 7 wherein the polymer coating is affixed to both the metal material and the hydrophilic coating, providing adhesion of the hydrophilic coating to the distal section of the FP coated core wire.

10. The method according to claim 7 wherein the hydrophilic coating comprises polyvinylpyrrolidones, polyethylene oxides, polyacrylates or a mixture thereof.

11. The method according to claim 7, wherein the hydrophilic coating adjoins the FP coating at an edge that forms a radial step.

12. The method according to claim 1, wherein the polymer coating has a predetermined outer diameter.

* * * * *